(12) United States Patent
Hughes

(10) Patent No.: US 9,072,909 B1
(45) Date of Patent: Jul. 7, 2015

(54) IMPLANTABLE MEDICAL ELECTRICAL LEAD CONNECTORS, ASSEMBLIES THEREOF, AND METHODS OF MANUFACTURE

(71) Applicant: Medtronic, Inc., Minneapolis, MN (US)

(72) Inventor: Jonathan A Hughes, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 17 days.

(21) Appl. No.: 14/132,211

(22) Filed: Dec. 18, 2013

(51) Int. Cl.
| | |
|---|---|
| H01R 24/04 | (2006.01) |
| A61N 1/375 | (2006.01) |
| H01R 13/516 | (2006.01) |
| H01R 43/24 | (2006.01) |
| A61N 1/05 | (2006.01) |

(52) U.S. Cl.
CPC ............ *A61N 1/3752* (2013.01); *H01R 13/516* (2013.01); *H01R 43/24* (2013.01); *A61N 1/056* (2013.01)

(58) Field of Classification Search
CPC ....................................................... H01R 24/58
USPC .................................................. 439/669, 909
See application file for complete search history.

(56) References Cited

U.S. PATENT DOCUMENTS

| | | | |
|---|---|---|---|
| 5,304,219 A | 4/1994 | Chernoff et al. | |
| 5,376,206 A * | 12/1994 | Maurer et al. | 156/242 |
| 7,108,549 B2 | 9/2006 | Lyu et al. | |
| 7,175,478 B2 * | 2/2007 | Ollivier | 439/669 |
| 7,187,974 B2 | 3/2007 | Haeg et al. | |
| 7,241,180 B1 * | 7/2007 | Rentas Torres | 439/668 |
| 7,274,963 B2 | 9/2007 | Spadgenske | |
| 7,326,083 B2 * | 2/2008 | Mehdizadeh et al. | 439/909 |
| 7,395,116 B2 | 7/2008 | Mehdizadeh et al. | |
| 7,551,967 B1 | 6/2009 | Karicherla et al. | |
| 7,647,110 B2 | 1/2010 | Hornfeldt et al. | |
| 7,648,401 B2 * | 1/2010 | Guenther et al. | 439/669 |
| 7,822,476 B2 | 10/2010 | Bartels et al. | |
| 8,911,265 B2 * | 12/2014 | Maio et al. | 439/669 |
| 2008/0234778 A1 | 9/2008 | Rebentisch | |
| 2008/0303728 A1 | 12/2008 | Lee et al. | |

(Continued)

FOREIGN PATENT DOCUMENTS

CN 102210901 A 12/2011

OTHER PUBLICATIONS (PCT/US2014/070444) PCT Notification of Transmittal of the International Search Report and the Written Opinion of the International Searching Authority.

*Primary Examiner* — Tho D Ta
(74) *Attorney, Agent, or Firm* — Michael C. Soldner

(57) ABSTRACT

An implantable lead connector assembly includes core and contact circuits held together and isolated from one another by insulation. The core circuit includes a conductive core and a conductor pin, which has a proximal end coupled to an outer surface of the core, and a distal end spaced outward from the outer surface and protruding distally from the insulation. Insulation sealing surfaces extend on either side of an outer contact surface of each contact circuit, and the sealing and contact surfaces define a uniform outer diameter of the assembly. A conductor pin of each contact circuit has a proximal end coupled to an inner surface of a contact ring of the corresponding circuit, and a distal end that protrudes distally from the insulation. The insulation may be formed by injection molding, and then outer surfaces of the molded insulation and contact ring(s) are ground down to the uniform outer diameter.

23 Claims, 12 Drawing Sheets

(56) References Cited

U.S. PATENT DOCUMENTS

| | | |
|---|---|---|
| 2011/0065301 A1 | 3/2011 | Boyd et al. |
| 2011/0137414 A1 | 6/2011 | Litzke et al. |
| 2011/0159748 A1 | 6/2011 | Lim et al. |
| 2012/0019260 A1 | 1/2012 | Reddy et al. |
| 2012/0053646 A1 | 3/2012 | Brase et al. |
| 2012/0151765 A1 | 6/2012 | James et al. |
| 2012/0239124 A1 | 9/2012 | Fan et al. |
| 2012/0322317 A1 | 12/2012 | Seeley et al. |

* cited by examiner

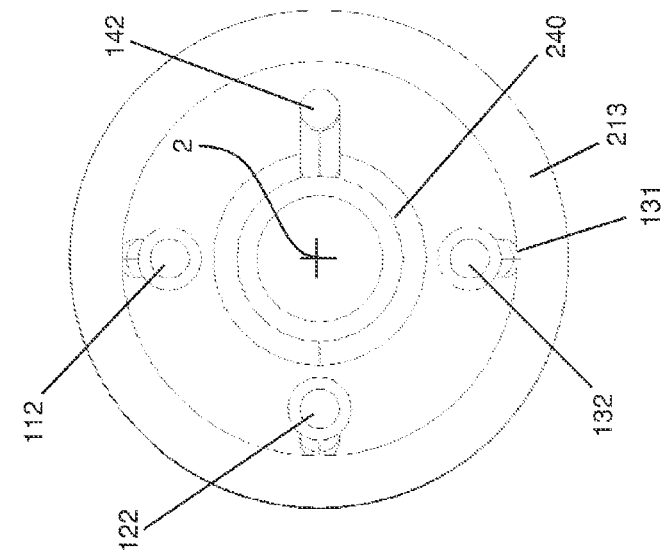
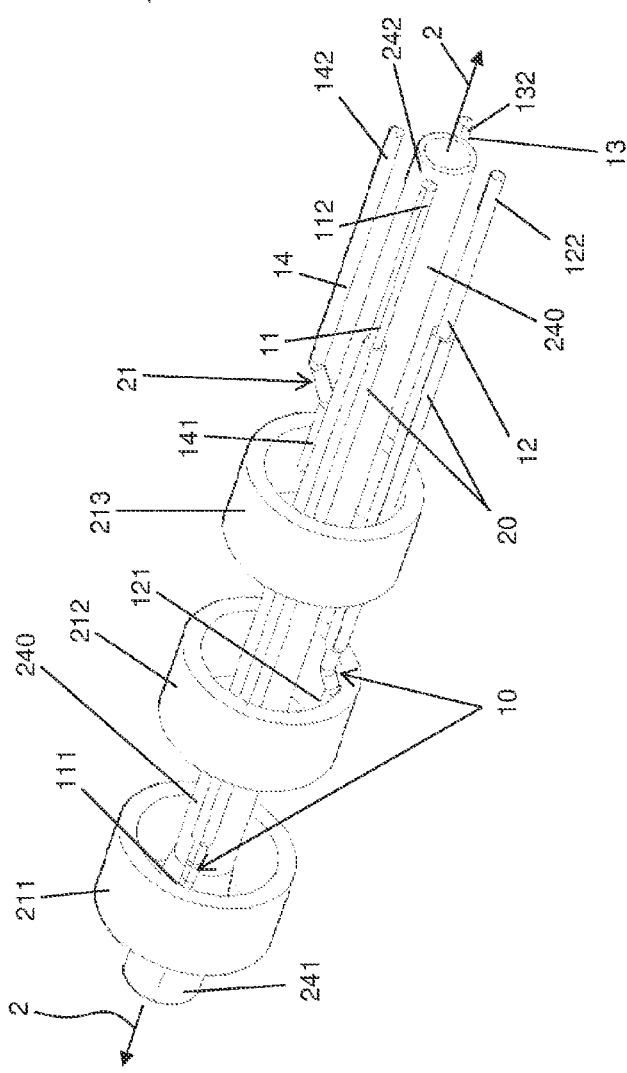

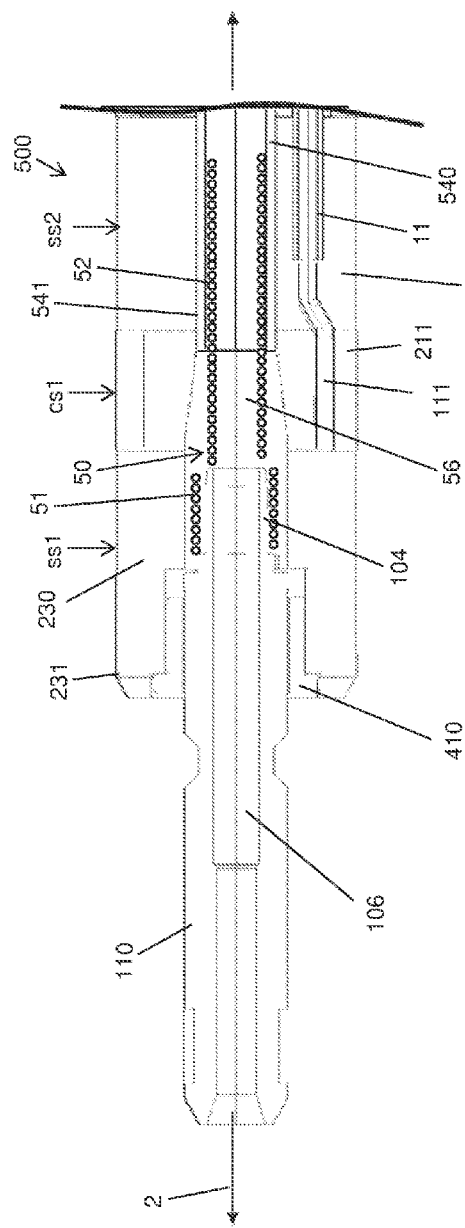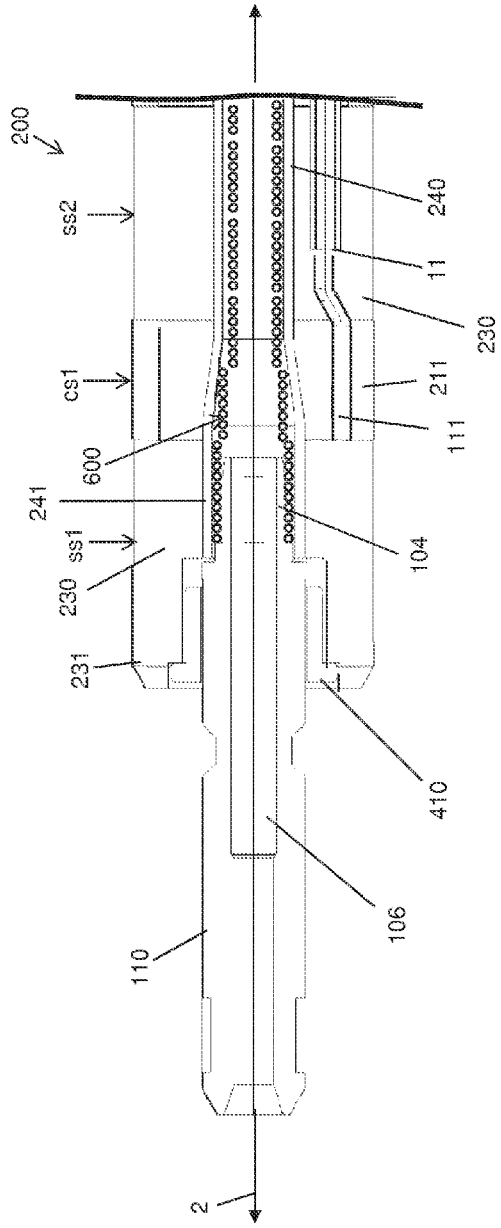
FIGURE 5
FIGURE 6

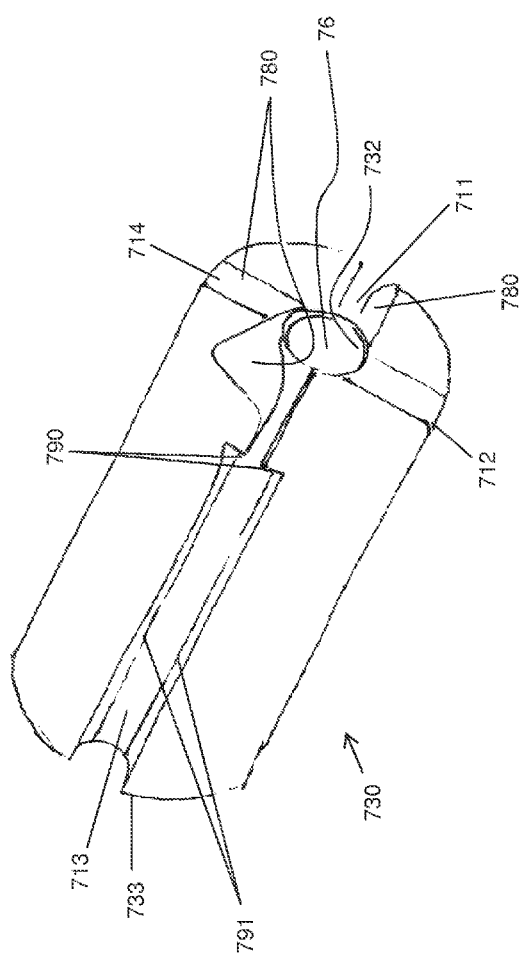
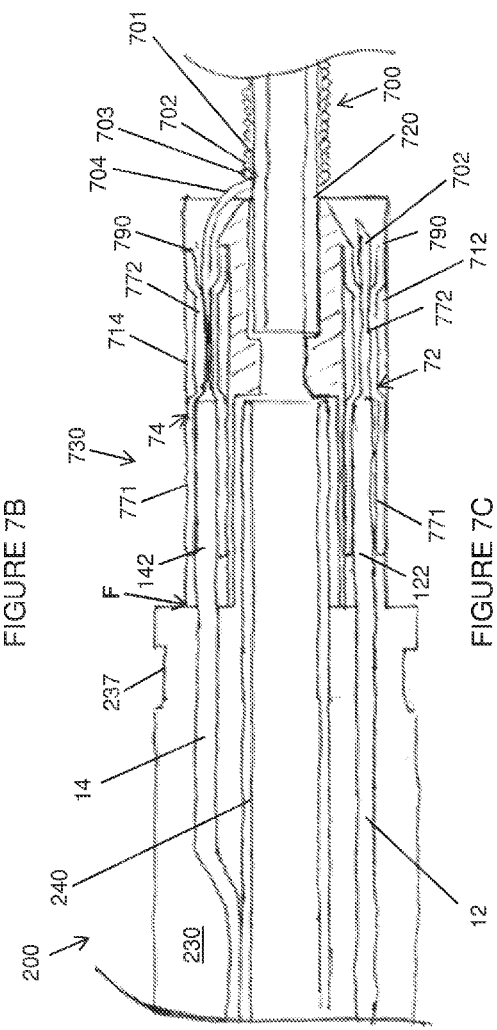
FIGURE 7B
FIGURE 7C

IMPLANTABLE MEDICAL ELECTRICAL LEAD CONNECTORS, ASSEMBLIES THEREOF, AND METHODS OF MANUFACTURE

FIELD OF THE DISCLOSURE

The present disclosure pertains to implantable medical electrical leads, and more particularly to constructions of, and manufacturing methods for lead connectors that are configured to mate with connector receptacles of implantable medical devices.

BACKGROUND

Implantable medical systems, for example, those providing electrical stimulation for cardiac or neurological therapy, often include a pulse generator device and an elongate medical electrical lead that extends from the device to a stimulation site in a body of a patient. Numerous configurations of implantable medical electrical lead connectors have been disclosed over the years, many of which are directed toward compliance with international industry standards; these standards specify essential dimensions and performance requirements to assure compatibility of connection between pulse generator device connector receptacles and lead connectors among a variety of manufacturers. One such standard dictates the form for a four-pole in-line connector of cardiac pacing and defibrillation leads and is commonly known as the IS-4, or in some cases, the DF-4 standard.

FIG. 1 is a schematic with a corresponding chart that describes various configurations of an exemplary implantable medical electrical lead 100. Lead 100 includes a connector 120 in conformance with the aforementioned IS-4 standard. FIG. 1 illustrates connector 120 including a terminal connector pin 110, three contact surfaces cs1, cs2, cs3, and four sealing surfaces ss1, ss2, ss3, and ss4, wherein, according to the IS-4 standard, pin 110 and first contact surface cs1 are low voltage contacts, and second and third contact surfaces cs2, cs3 are high voltage contacts. The IS-4 standard also requires a specific configuration of terminal connector pin 110 and a uniform outer diameter D of connector 120. Those skilled in the art understand that pin 110 and contact surfaces cs1-cs3 are configured to mate with device contacts mounted within a connector receptacle of the device, and sealing surfaces ss1-ss4 are configured to mate with sealing rings, which are interspersed between the contacts within the device connector receptacle, so that an electrical coupling is made between each device contact and the corresponding pin/contact surface, within the receptacle, and these couplings are electrically isolated from one another by the sealing rings.

FIG. 1 further illustrates lead 100 including an elongate body 130, which extends distally from connector 120 to a low voltage distal-most electrode de, two types of which are shown: one for what is known as a passive fixation lead (designated 'P'), and the other for what is known as an active fixation lead (designated 'A'). Although not shown, those skilled in the art understand that lead body 130 includes an elongate conductor extending therein, which couples distal-most electrode de, of either type of lead 100, to terminal connector pin 110, wherein, if lead 100 is the active fixation type A, rotation of pin 110 is translated, via the conductor, to electrode de, which is formed as a helix for fixation in tissue at a target implant site. If lead 100 is the passive fixation type P, electrode de may be held at the target implant site via tines 135. Each type of lead 100 may further include one or more of electrodes e1, e2, e3, which are shown mounted around lead body 130, wherein body 130 further includes a corresponding one or more elongate conductors (not shown), for example, to couple electrode e1 to contact surface cs1, to couple electrode e2 to contact surface cs2, and to couple electrode e3 to contact surface cs3. It should be noted that lead body 130 further includes insulative tubing that isolates the elongate conductors from one another. Various suitable configurations and constructions for each of electrodes de, e1-e3 are well known to those skilled in the art.

Either type of lead 100 may be configured according to any of the four exemplary configurations outlined in the chart of FIG. 1. In the first configuration, lead 100 includes just electrodes de and e1, wherein e1 is employed for pacing and sensing, in combination with electrode de, and for defibrillation, in which case electrode e1 is coupled to both first and second contact surfaces cs1, cs2 of connector 120. In the second configuration, lead 100 includes electrodes de, e1, and e3, wherein electrodes de and e1 function the same as in the first configuration, and electrode e3 is also employed for defibrillation, being coupled to contact surface cs3. In the third configuration, lead 100 again includes electrodes de, e1, and e2, but electrode e1 is only employed for pacing and sensing, so is not coupled to contact surface cs2, instead electrode e2 is coupled to contact surface cs2. In the fourth configuration, lead 100 includes all of the illustrated electrodes de, e1-e3, wherein e1 is solely employed for pacing and sensing, and electrodes e2 and e3 are solely employed for defibrillation.

Although only the fourth configuration employs all of electrodes e1-e3, the aforementioned IS-4 industry standard requires the presence of all contact surfaces cs1-cs3 and all sealing surfaces ss1-ss4 for the other three configurations, even though contact surface cs3 may be inactive, to preserve the standard form of connector 120. Furthermore, it should be noted that the IS-4 industry standard also applies to low voltage only lead connectors, which have the same form as connector 120, but contact surfaces cs-2 and cs3 are designated for low voltage electrodes. Thus, a modular assembly for lead connector 120 is desirable, to increase the flexibility in manufacturing a variety of implantable medical electrical lead configurations, of both the active fixation type A and passive fixation type P. Even though some constructions of lead connectors that incorporate modular assemblies, are known in the art, there is still a need for new constructions and manufacturing methods.

SUMMARY

Implantable medical electrical lead connectors and connector assemblies thereof, according to embodiments described herein, conform to one or more requirements, for example, of an industry standard. An assembly for some connector embodiments is modular to allow the construction thereof independent of a particular lead type and/or configuration, then the assembly may be incorporated by any one of a number of lead types and configurations, for example, like the types and configurations described above.

According to some embodiments, an assembly for a lead connector includes a core circuit, a contact circuit, which has an outer contact surface, and a bulk of insulation, which holds together the core and contact circuits and isolates the circuits from one another, and which includes an outer surface divided into sealing surfaces that extend on either side of the contact surface. The core circuit includes a conductive core, which extends along a central longitudinal axis of the assembly, and a conductor pin, which has a proximal end coupled to an outer surface of the core, and a bend formed between the proximal end and a remainder of the pin such that the remainder is spaced outward from the outer surface of the core. The contact circuit includes a contact ring, which extends around the conductive core and whose outer surface forms the aforementioned contact surface, and a conductor pin, which has a proximal end coupled to an inner surface of the contact ring. In some embodiments, the conductor pin that is coupled to the contact ring also has a bend formed between the proximal end thereof and a remainder of the pin such that the remainder is spaced inward from the inner surface of the contact ring. According to some preferred embodiments, an assembly includes three of the above-described contact circuits such that the outer surfaces of the contact rings form separate contact surfaces spaced apart from one another by the sealing surfaces of the bulk of insulation.

A distal end of each conductor pin of the assembly protrudes distally from a distal end of the bulk of insulation, and the distal ends of the pins are spaced apart from one another and spaced approximately equidistant from the central longitudinal axis of the assembly. In some embodiments, couplings between lead body conductors and the distal ends of the conductor pins are facilitated by a transition fitting, which is joined to the bulk of insulation, wherein a distal end of the conductive core is received within a lumen of the fitting, and the distal end of each conductor pin is supported in a peripheral groove of the fitting.

A connector that includes an assembly like those described above, further includes a terminal connector pin, which is part of the core circuit and protrudes proximally from a proximal end of the bulk of insulation. According to some embodiments, the terminal connector pin includes a shank that is engaged within a lumen of the assembly for coupling to the conductive core. The lumen may be formed through the conductive core and have a multi-point contact mounted therein, wherein the multi-point contact engages with the shank of the terminal connector pin.

According to some manufacturing methods disclosed herein, after forming each of the above-described circuits, the circuits are assembled together with a mold assembly. The mold assembly includes a cavity and a core plug, wherein the contact ring of each contact circuit is positioned in a corresponding recessed groove of the cavity, the conductive core of the core circuit is positioned within a perimeter of each contact ring, the core plug is positioned in the cavity at a location spaced apart from each recessed groove, and the distal ends of the conductor pins and the conductive core are inserted into corresponding bores of the core plug. The core plug, in addition to the bores that support the distal ends of conductor pins and conductive core, includes gates through which an insulative material is injected, according to some preferred methods, to form a molded assembly of the above-described bulk of insulation and the contact circuits. Following the injection molding process, an outer surface of the molded assembly is ground down, for example, via a centerless grinding process, to the uniform outer diameter.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIGS. 2B-C are a perspective view and an end view, respectively, of a subassembly for the lead connector assembly, according to some embodiments of the present invention;

FIG. 5 is a cross-section view through a proximal end of a lead connector, according to some alternate embodiments;

FIG. 6 is a cross-section view through a proximal end of a lead connector, according to yet further embodiments;

FIG. 7B is a perspective view of a transition fitting of the lead connector assembly, according to some embodiments;

FIG. 7C is a cross-section view through the transition fitting portion of the assembly of FIG. 7A, according to some embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
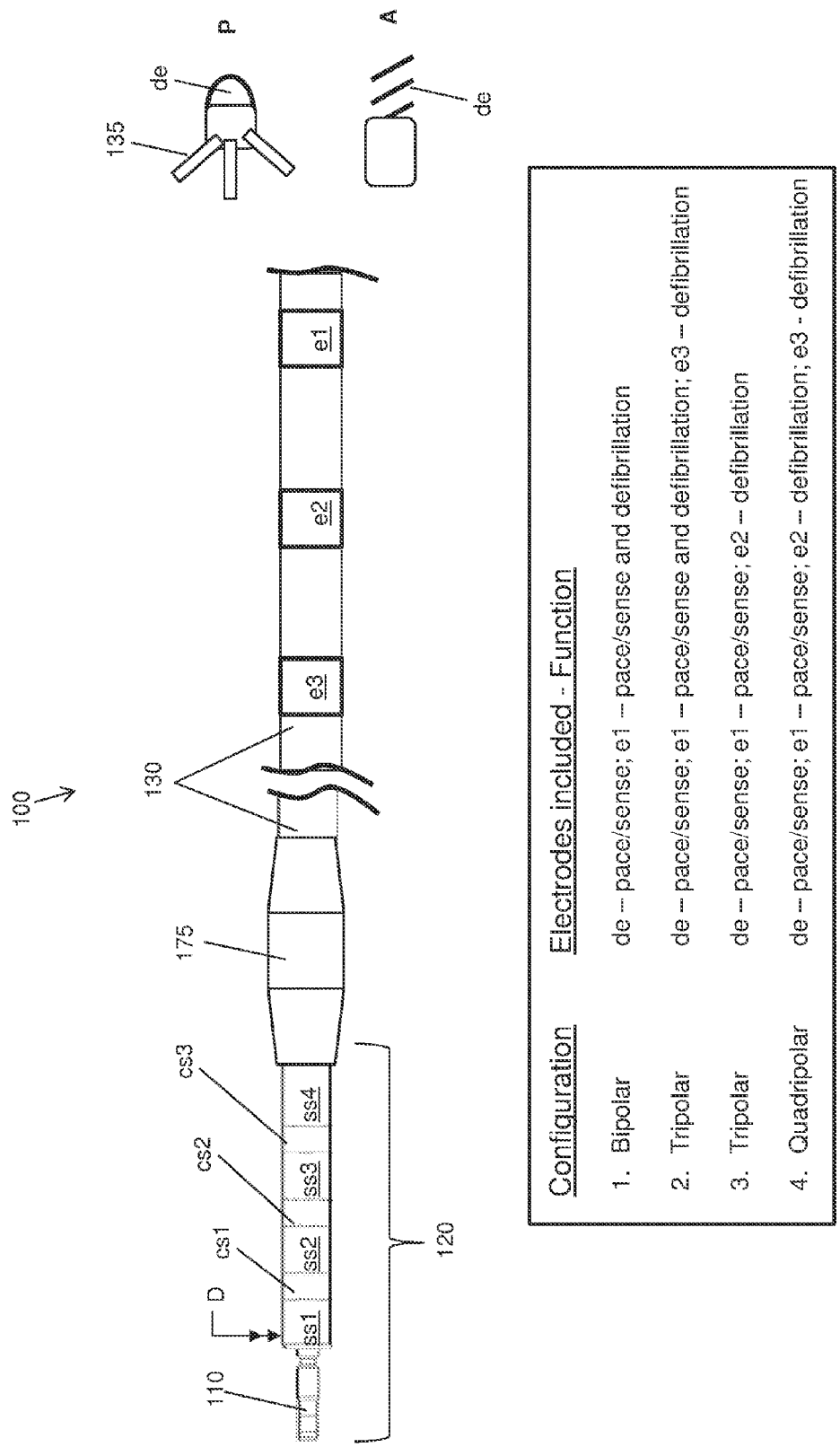
FIG. 1 is a schematic with a corresponding chart that describes various configurations of an exemplary implantable medical electrical lead.
Figure 2A:
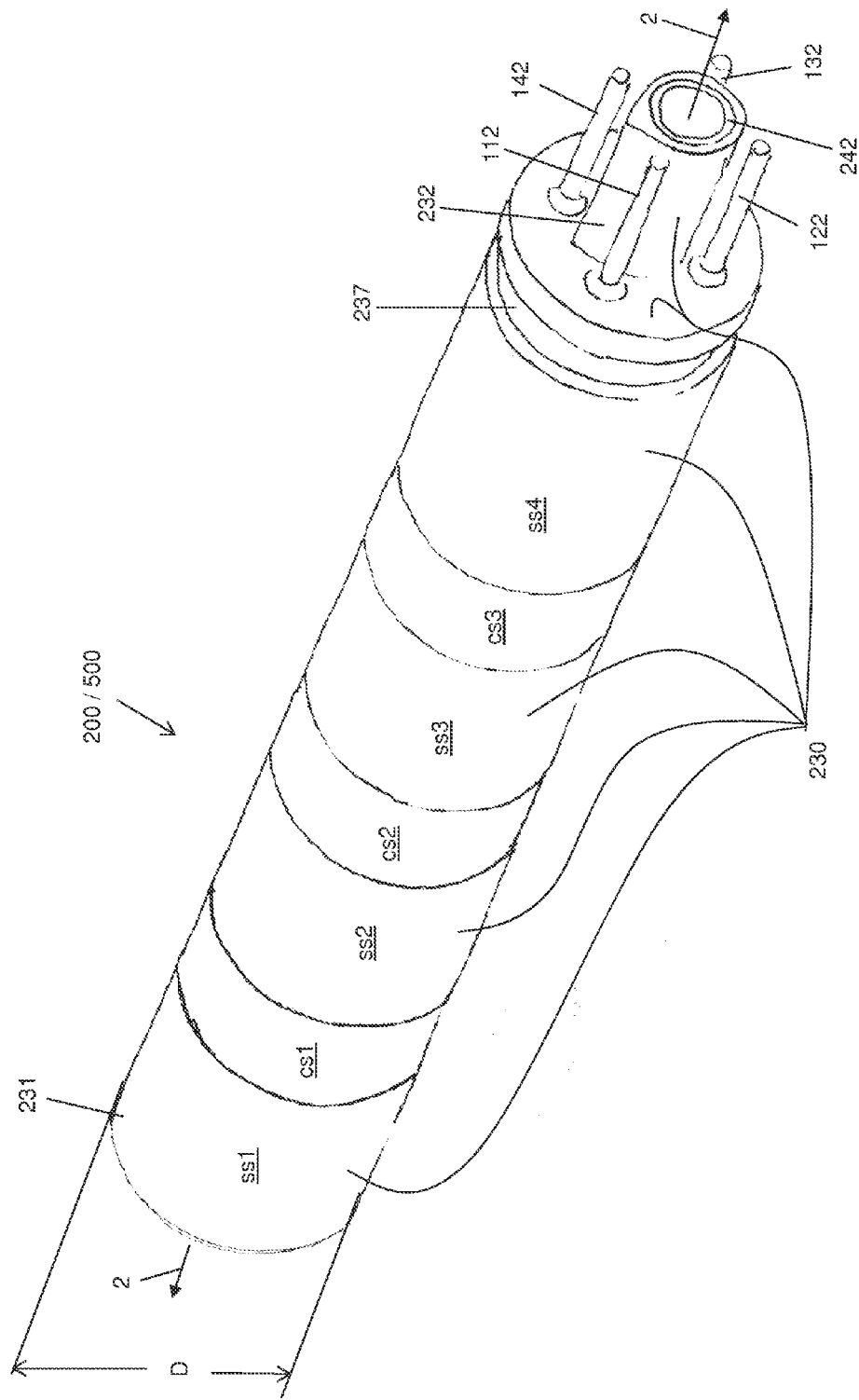
FIG. 2A is a perspective view of an implantable medical electrical lead connector assembly, according to some embodiments.

FIG. 2A is a perspective view of an implantable medical electrical lead connector assembly 200, according to some embodiments; and FIGS. 2B-C are a perspective view and an end view, respectively, of a subassembly for connector assembly 200, according to some embodiments, wherein first, second, and third contact rings 211, 212, 213 extend around a conductive core 240, and correspond to first, second, and third contact surfaces cs1, cs2, cs3, respectively. FIG. 2A illustrates assembly 200 including a central longitudinal axis 2, and having the aforementioned uniform outer diameter D that conforms to a requirement for a connector, in which assembly 200 is included (e.g., connector 120 of FIG. 1), to mate with a connector receptacle of an implantable medical device. FIG. 2A further illustrates assembly 200 including a bulk of insulation 230, which includes an outer surface divided into the above-described four sealing surfaces ss1, ss2, ss3, ss4. Insulation 230 extends around conductive core 240 and between contact surfaces cs1, cs2, cs3, and distal ends 112, 122, 132, 142 of conductor pins 11, 12, 13, 14 protrude distally therefrom. Bulk of insulation 230 may be formed from any suitable relatively hard, insulative, medical grade polymer material, and example of which is a 75D durometer thermoplastic polyurethane. FIG. 2B illustrates conductive core 240 extending from a proximal end 241 thereof to a distal end 242 thereof, along axis 2, wherein a proximal end 141 of conductor pin 14 is coupled to an outer surface of core 240, for example, by laser welding, to form a core circuit to which a terminal connector pin, for example, the above-described connector pin 110 (FIG. 1) may be coupled. A bend 21 is shown formed in pin 14, between the coupled proximal end 141 thereof an a remainder of pin 14, such that the remainder of pin 14, including distal end 142, is spaced outward from the outer surface of core 240. FIGS. 2B-C illustrate a proximal end 111, 121, 131 of each of the three other conductor pins 11, 12, 13 of the subassembly coupled to an inner surface of a corresponding ring 211, 212, 213, for example, by laser welding, to form three contact circuits. With reference to the end view of the subassembly in FIG. 2C, distal ends 112, 122, 132, 142 of conductor pins 11, 12, 13, 14 are spaced apart from one another and spaced approximately equidistant from central longitudinal axis 2, according to some preferred embodiments.

With further reference to FIG. 2B, each of conductor pins 11, 12, 13, like pin 14, has a bend 10 formed therein, between the coupled proximal end 111, 121, 131, and a remainder thereof, such that the remainder of each pin 11, 12, 13, including the corresponding distal end 112, 122, 132, is spaced inward from the inner surface of the corresponding contact ring 211, 212, 213, for example, to achieve the above-described spacing shown in FIG. 2C. However, according to some alternate embodiments, the inner surface of each contact ring 211, 212, 213 may be configured such that the coupling of the proximal end 111, 121, 131 of the corresponding pin 11, 12, 13 thereto spaces the remainder of the corresponding pin inward, and each bend 10 is not necessary. According to an exemplary embodiment, conductive core 240 is formed from medical grade stainless steel tubing, each ring 211, 212, 213 is formed from MP35N alloy, and each conductor pin 11, 12, 13, 14 is formed from a relatively rigid MP35N alloy wire. An optional jacket 20 of insulation is shown formed about pins 11, 12, 13 between the corresponding proximal and distal ends thereof.

Figure 3A:
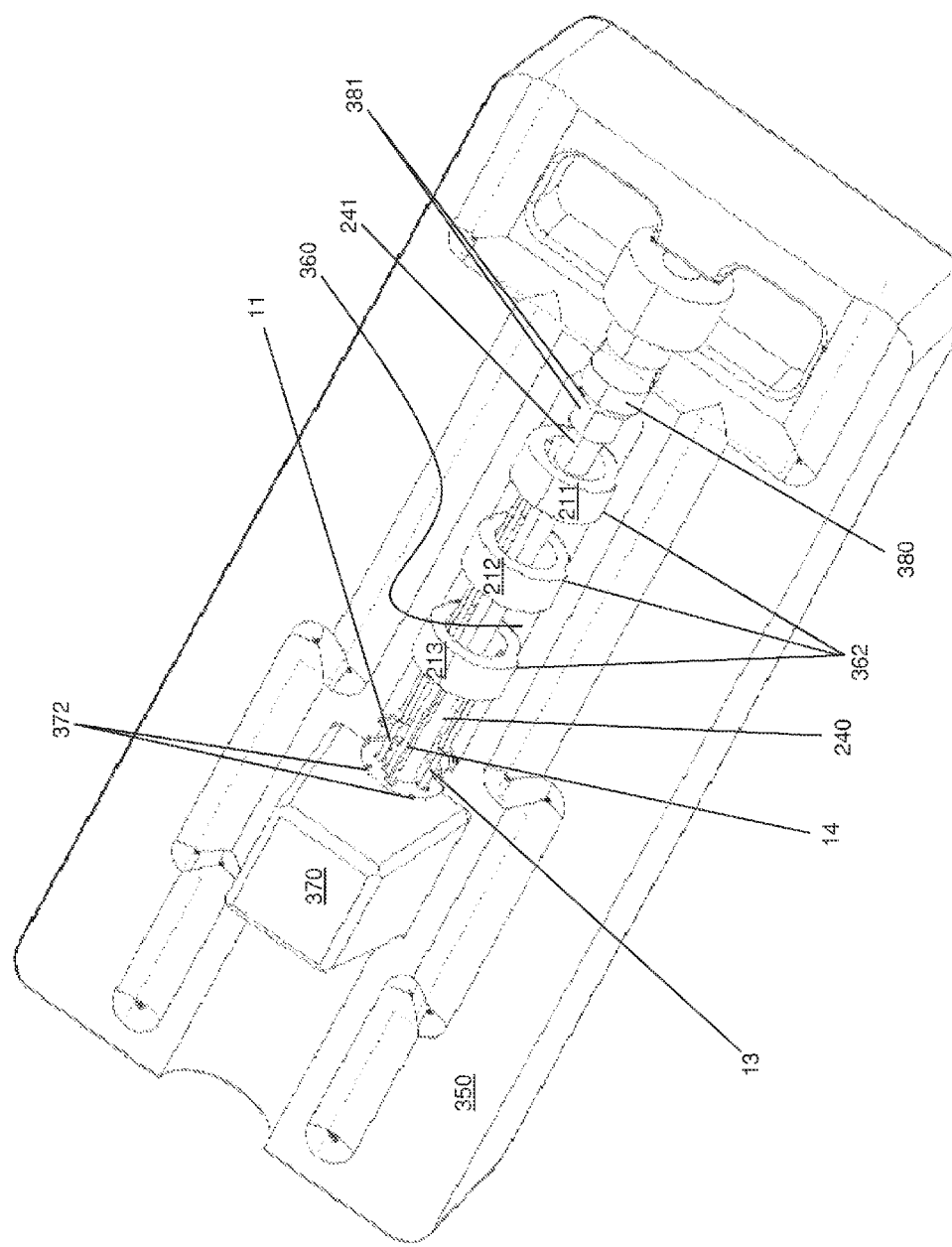
FIG. 3A is a perspective view of the subassembly assembled together with a mold assembly, according to some methods of the present invention.

With reference back to FIG. 2A, according to some preferred embodiments, bulk of insulation 230 is formed by injection molding the insulative material around the subassembly shown in FIG. 2B. FIG. 3A is a perspective view of the above-described contact and core circuits of the subassembly assembled together with a mold assembly, according to some methods of the present invention. It should be noted that only one of two opposing and confronting mold blocks 350 is shown in FIG. 3A. FIG. 3A illustrates each contact ring 211, 212, 213 positioned in a corresponding recessed groove 362 of a cavity 360 formed in each mold block 350 of the mold assembly, with distal ends 112, 122, 132, 142 of conductor pins 11, 12, 13, 14 (FIG. 2B) inserted into corresponding bores of a core plug 370 of the mold assembly. (The opposing mold block, which is not shown, includes the other, opposing, portion of cavity 360.) Conductive core 240 is shown positioned within a perimeter of each ring 211, 212, 213 in cavity 360, with distal end 242 (FIG. 2B) of core 240 inserted within another bore of core plug 370. With further reference to FIG. 2A, it may be appreciated that this other bore of core plug 370 has an asymmetric profile so that a distal end 232 of insulation 230, which is formed around distal end 242 of core 240 has the asymmetric profile (e.g., a tear drop shape) that is shown in FIG. 2A, according to some embodiments.

Figure 3B:
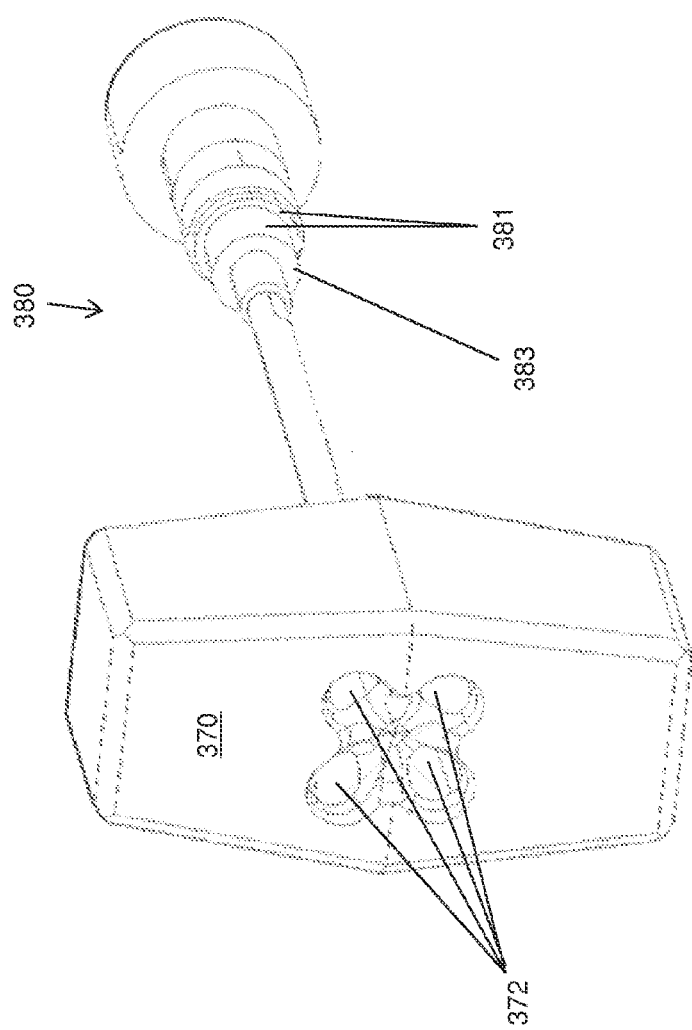
FIG. 3B is a perspective view of portions of the mold assembly, according to some embodiments.

FIG. 3A further illustrates core plug 370 including injection gates 372 formed therein to receive the flow of the insulative material therethrough; and, in FIG. 3B, openings of gates 372 may be seen on an opposite side of core plug 370. When the insulative material is injected through gates 372 and into cavity 360, around the core and contact circuits assembled therein, each recessed groove 362 prevents the corresponding contact ring 211, 212, 213 from being moved by the force of the flow of the injection, and a core pin 380 of the mold assembly, which extends within conductive core 240, prevents the movement of conductive core 240, and provides a shut-off at either end 241, 242 of core 240. FIG. 3B is a perspective view of core pin 380 and core plug 370 separated from the rest of the mold assembly. FIG. 3B illustrates core pin 380 including a shoulder 383, against which proximal end 241 of conductive core 240 abuts, as shown in FIG. 3A, and an enlarged stepped portion 381, which extends proximally from shoulder 383.

Figure 3C:
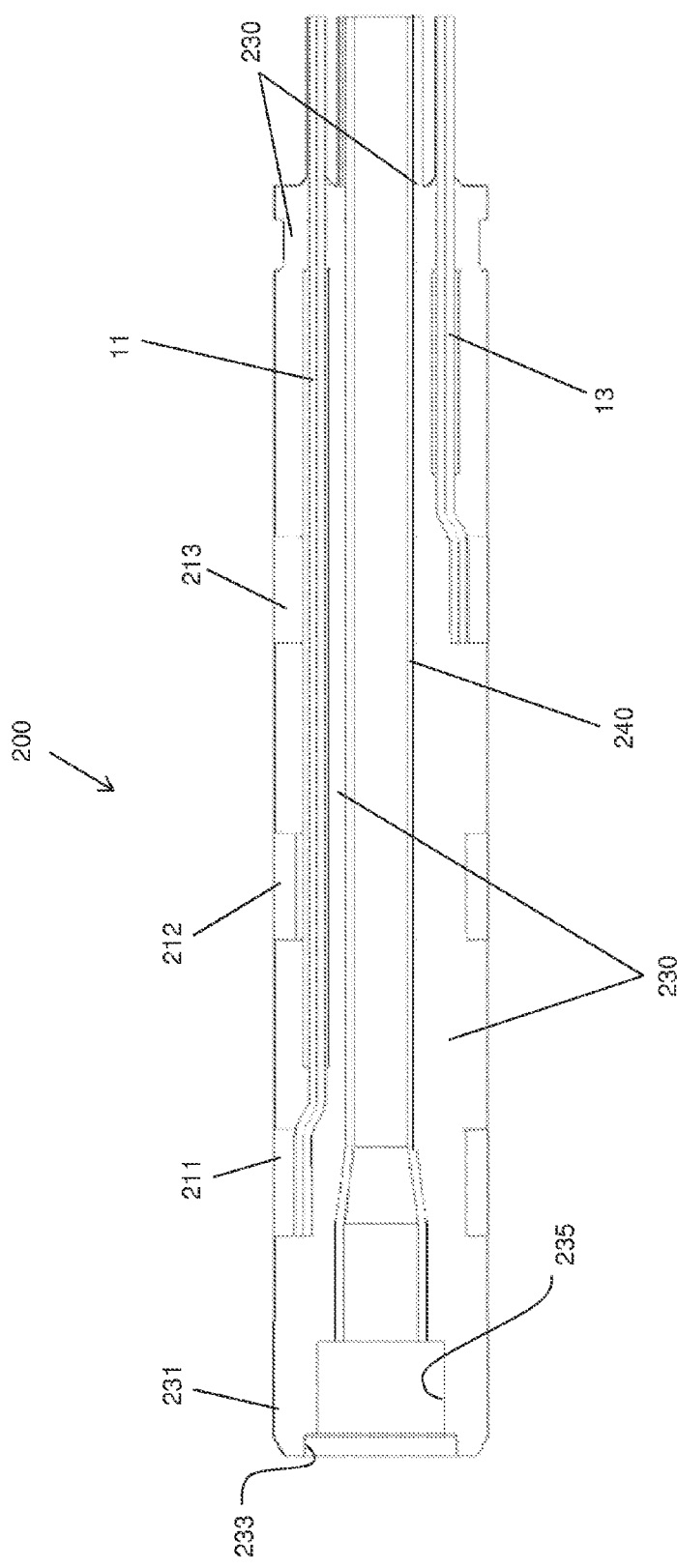
FIG. 3C is a cross-section view through the assembly of FIG. 2A, according to some embodiments.

With reference to FIG. 3C, which is a cross-section view through assembly 200, it may be appreciated that the molded bulk of insulation 230 holds together the core and contact circuits and isolates the core and contact circuits from one another. Furthermore, enlarged stepped portion 381 of core pin 380 creates a bore 235 and counter bore 233 opening in insulation bulk 230, at a proximal end 231 thereof, which accommodates a retainer component 410 that holds terminal connector pin 110 in place, relative to assembly 200, according to some embodiments, for example, like that illustrated in FIG. 4A.

To facilitate holding rings 211, 212, 213 in recessed grooves 362 of mold cavity 360, according to the above-described method, each contact ring 211, 212, 213 has an enlarged outer diameter, relative to the injection molded material; so, a manufacturing step to reduce the outer diameter of rings 211, 212, 213, and, in some cases, to also remove molding byproducts at the outer diameter of the injection molded material (e.g., parting line removal), follows the injection molding. According to some methods, a grinding method, for example, a centerless grinding process known to those skilled in the art, is employed to bring the outer diameter of the molded assembly, along an entire length of contact surfaces cs1-cs3 and sealing surfaces ss1-ss4, down to the uniform outer diameter D shown in FIG. 2A.

With further reference to FIG. 2A, assembly 200, being modular, may be incorporated by any one of a number of lead types and configurations, for example, like the types and configurations described above in conjunction with FIG. 1. With reference to FIG. 1, if assembly 200 is employed by lead 100 of the passive fixation type P, terminal connector pin 110 may be an element of the core circuit—coupled to conductive core 240, which is coupled to conductor pin 14, for example, in the manner described below in conjunction with FIGS. 4A-B, wherein each elongate conductor of the lead is coupled to a corresponding conductor pin distal end 112, 122, 132, 142, to electrically couple each electrode de, e1, e2, e3 to connector 120. Or, a modified assembly 200 may be employed in the manner described in conjunction with FIG. 5. If assembly 200 is employed by lead 100 of the active fixation type A, the coupling of each contact surface cs1, cs2, cs3 to a corresponding electrode e1, e2, e3 is accomplished via the coupling of the corresponding conductor pin distal end 112, 122, 132 to the corresponding lead conductor, but the lead conductor that is coupled to distal-most electrode de (e.g., a helix electrode) is directly coupled to terminal connector pin 110, for example, as described below in conjunction with FIG. 6. For either type of lead, a transition fitting, several embodiments of which will be described below in conjunction with FIGS. 7A-9, may be joined to bulk of insulation 230 to support conductor pin distal ends 112, 122, 132, 142 and associated couplings thereof to the lead conductors. With further reference to FIG. 2A, in conjunction with FIG. 1, an external groove 237 is formed in insulation bulk 230, just distal to fourth sealing surface ss4, to accommodate coupling of a connector sleeve 175, for example, formed from medical grade silicone rubber, that extends from lead body 130 to connector 120.

Figure 4A:
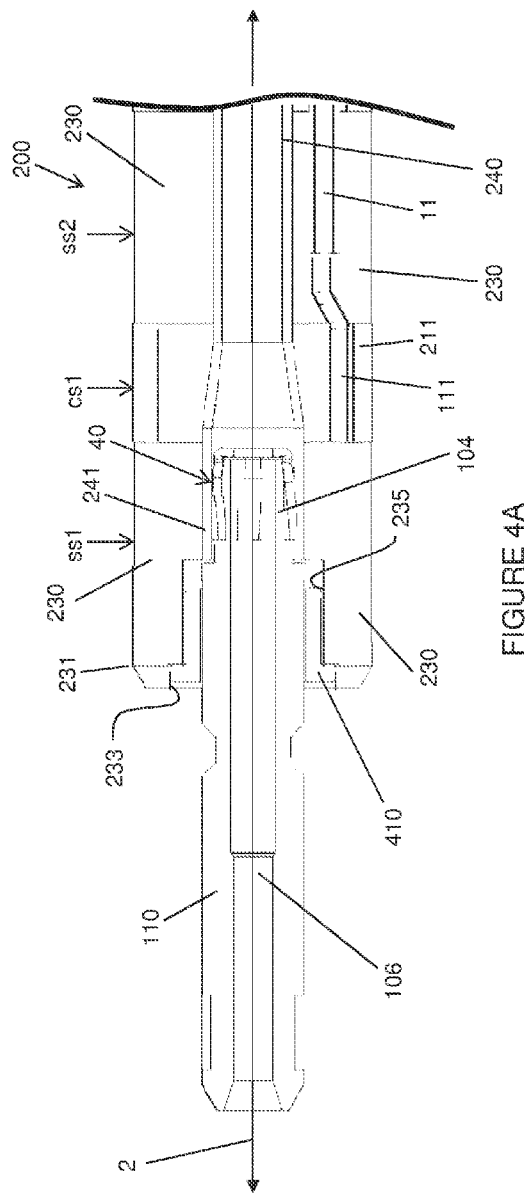
FIG. 4A is a cross-section view through a proximal end of a lead connector, according to some embodiments.
Figure 4B:
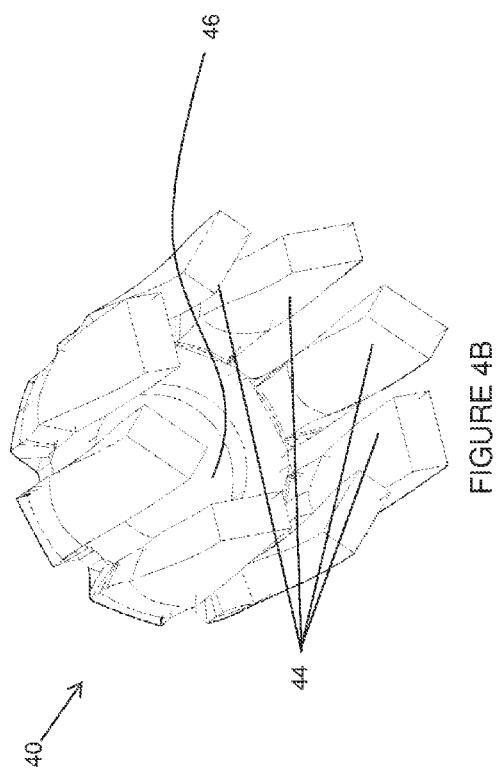
FIG. 4B is a perspective view of a multi-point contact employed in the assembly of the lead connector of FIG. 4A, according to some embodiments.

FIG. 4A is a cross-section view through a proximal end of a lead connector that includes assembly 200, according to some embodiments. FIG. 4A illustrates the core circuit of assembly 200 including terminal connector pin 110, which is coupled to conductive core 240. According to the illustrated embodiment, proximal end 241 of conductive core 240 defines a lumen in which a multi-point contact 40 is mounted, and multi-point contact 40 engages a shank 104 of connector pin 110, within the lumen of proximal end 241, to couple connector pin 110 to conductive core 240. FIG. 4B is a perspective view of multi-point contact 40, according to some embodiments. FIG. 4B illustrates multi-point contact 40 including a plurality of spring-loaded fingers 44 spaced apart around an aperture 46 of contact 40. With reference to FIG. 4A, aperture 46 is approximately aligned along central axis 2, when multi-point contact 40 is press fit within the lumen of conductive core 240, so that fingers 44 create multiple contact points between shank 104 and conductive core 240. According to an exemplary embodiment, multi-point contact 40 is formed from a sheet of MP35N alloy having a thickness of approximately 0.005 inch, for example, by a stamping process. FIG. 4A further illustrates terminal connector pin 110 including a through lumen 106 that is in fluid communication with the lumen of conductive core 240, via aperture 46 of multi-point contact 40, for example, to allow passage of an instrument, such as a stylet, therethrough and into a lumen of lead body 130 (FIG. 1).

FIG. 5 is a cross-section view through a proximal end of a lead connector, according to some alternate embodiments, which includes a modular assembly 500. With reference back to FIG. 2A, assembly 500 has the same external configuration as assembly 200, and may be manufactured in approximately the same manner, as described in conjunction with FIGS. 3A-B, but the core circuit of assembly 500 includes a different configuration of conductive core 240. With reference to FIG. 5, a proximal end 541 of a conductive core 540 in assembly 500 is not flared like proximal end 241 of conductive core 240, and conductive core 540 has a shorter length, along axis 2, than core 240. FIG. 5 illustrates the core circuit of assembly 500 including terminal connector pin 110 coupled to conductive core 540 by a coil-type multi-point contact 50, wherein contact 50 includes a distal portion 52, which is fitted within a lumen defined by proximal end 541 of conductive core 540, and a proximal portion 51 that extends proximally from proximal end 541 of conductive core 540 to engage shank 104 of connector pin 110. According to the illustrated embodiment, proximal portion 51 of contact 50 is mounted around shank 104, for example, having been spun thereon and welded thereto, and distal portion 52 of contact 50 is compressed within the lumen of conductive core 541 to create multiple contact points therewith. According to an exemplary embodiment, contact 50 is formed from an tight-wound MP35N wire that has a wire diameter of approximately 0.005 inch. FIG. 5 further illustrates a lumen 56 of contact 50 bridging lumen 106 of connector pin 110 and the lumen of conductive core 540, for example, to allow passage of an instrument therethrough as described above.

As mentioned above, the core circuit configurations associated with FIGS. 4A-5 may be employed by lead 100 of the passive fixation type P (FIG. 1), wherein, with reference back to FIG. 2A, distal-most electrode de is coupled to terminal connector pin 110, via an elongate conductor of the lead coupled to contact pin distal end 142 of the core circuit. FIG. 6 is a cross-section view through a proximal end of a lead connector, which includes assembly 200, according to embodiments that are suitable for employment by lead 100 of the active fixation type A. FIG. 6 illustrates an elongate coiled lead conductor 600 coupled to terminal connector pin 110, for example, being mounted around shank 104 and laser welded thereto, wherein conductor 600 extends distally from the lead connector and through lead body 130 to couple with distal-most electrode de, for example, of the helix type illustrated in FIG. 1 for active fixation type lead A. Thus, according to the embodiment of FIG. 6, conductor 600 couples distal-most electrode de to connector pin 110, without the core circuit interface employed by passive fixation type lead P, so as to form a drive shaft with connector pin 110, which may be rotated to extend and retract helix electrode de relative to lead body 130, according to constructions and methods known in the art.

Figure 7A:
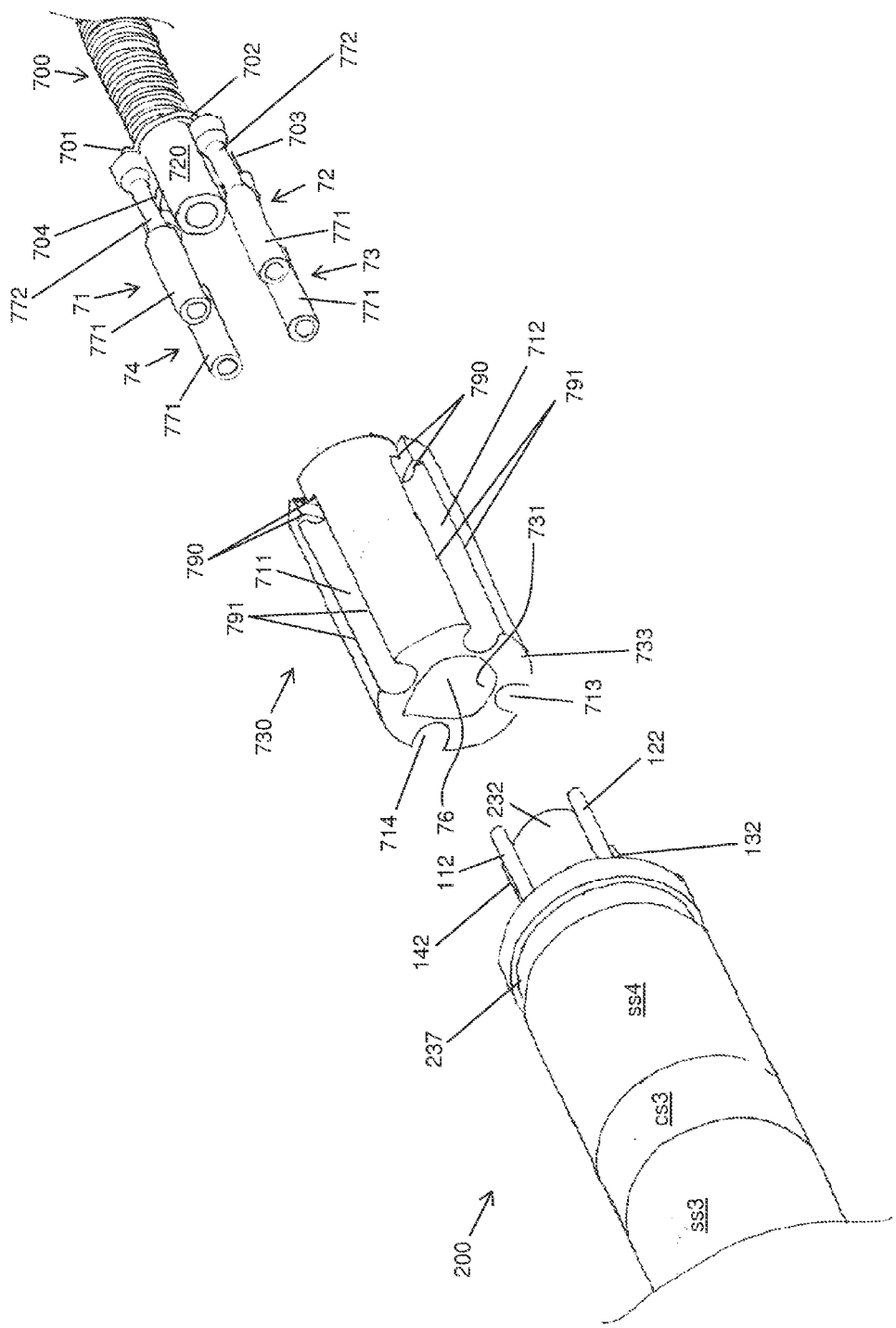
FIG. 7A is an exploded perspective view of a lead connector assembly, according to some embodiments.

FIG. 7A is an exploded perspective view of a connector assembly that includes assembly 200 and a transition fitting 730, according to some embodiments; and FIG. 7B is a perspective view of transition fitting 730, according to some embodiments. FIG. 7A illustrates transition fitting 730 including a lumen 76 and four peripheral grooves 711, 712, 713, 714, each of which is positioned and sized to support conductor pin distal ends 111, 112, 113, 114 when transition fitting 730 is joined to assembly 200, as illustrated in the cross-section view of FIG. 7C. Transition fitting 730 is preferably formed from the same insulative material that forms bulk of insulation 230 of assembly 200, and a proximal end 733 thereof may be fused to bulk of insulation 230 by a solvent or thermal process known in the art, for example, at an abutting interface F (FIG. 7C). A proximal portion 731 of lumen 76, seen in FIG. 7A, has an asymmetric profile to fit around the similar asymmetric profile of distal end 232 of insulation 230. These asymmetric profiles provide a keyed fit, for example, to guide proper alignment of grooves 711-714 with conductor pin distal ends 111, 112, 113, 114 when joining fitting 230 to assembly 200. FIGS. 7A and 7C also show a proximal portion of a lead body, for example, lead body 130 of lead 100 (FIG. 1), passive fixation type P, wherein a multi-conductor coil 700 thereof extends around an inner insulation tubing 720 thereof, and is configured for coupling to conductor pin distal ends 112, 122, 132, 142 of assembly 200. FIG. 7B shows a distal portion 732 of lumen 76, which is sized to receive inner insulation tubing 720, for example, as shown in FIG. 7C. Although not shown, it should be understood that lead body 130 also includes an outer insulation tubing that extends over coil 700 to isolate coil 700 from an environment external to lead 100.

FIG. 7A further illustrates multi-conductor coil 700 including at least four individual conductor coil filars 701, 702, 703, 704, for coupling electrodes e1, e2, e3, de, respectively, to the corresponding conductor pin distal end 112, 122, 132, 142, for example, to accommodate the fourth lead configuration (quadripolar) in the chart of FIG. 1. However, with further reference to the chart of FIG. 1, assembly 200 and transition fitting 730, being modular, can also be employed for any of the other three lead configurations. For example, in the second, tripolar configuration, lead conductor coil filar 704 couples distal-most electrode de to terminal connector pin 110 via a coupling with conductor pin 14, lead conductor coil filars 701 and 702 couple first electrode e1 to both first and second contact surfaces cs1, cs2, via couplings with conductor pins 11 and 12, and lead conductor coil filar 703 couples third electrode e3 to third contact surface cs3, via conductor pin 13. In the first, bipolar configuration, conductor pins 11, 12 and 14 of assembly 200 are employed in the same manner, but conductor pin 13 remains uncoupled so that third contact surface cs3 is inactive.

With further reference to FIGS. 7A and 7C, each conductor pin distal end 112, 122, 132, 142 may be coupled to the corresponding conductor coil filar 701, 702, 703, 704, within the corresponding groove 711, 712, 713, 714 of transition fitting 730, by means of a corresponding one of junction sleeves 71, 72, 73, 74. According to the illustrated embodiment, each junction sleeve 71-74 includes a crimp portion 772, each of which is shown crimped to the corresponding conductor coil filar 701-704, and a weld portion 771, each of which is configured to receive the corresponding conductor pin distal end 112, 122, 132, 142 therein, for laser welding thereto. According to an exemplary embodiment, each junction sleeve 71-74 is formed from MP35N alloy, and has an inner diameter of approximately 0.012 inch and an outer diameter of approximately 0.02 inch. With reference to FIG. 7B, in some embodiments, a distal entry into each groove 711-714 has a rounded edge 780 to provide strain relief for the corresponding conductor coil filar 701-704, just distal to the crimp thereof within the corresponding sleeve 71-74. According to some preferred embodiments, each groove 711-714 is further configured with tabbed opposing edges 791 and shoulders 790 that can help to retain each junction sleeve 71-74 in the corresponding groove 711-714. According to some methods, after crimping each sleeve 71-74 to the corresponding filar 701-704, each sleeve 71-74 may either be pushed radially, past the tabs of edges 791, and into the corresponding groove 711-714 for a snap fit therein, or slid into the corresponding groove 711-714 from proximal end 733 of transition fitting 730, for example, until each sleeve abuts shoulders 790 of the corresponding groove 711-714.

Following the coupling of each lead conductor to the corresponding contact pin of the connector assembly, the aforementioned connector sleeve 175 (FIG. 1) is assembled around the above-described couplings, for example, supported by transition fitting 730, and is secured to assembly 200 by interlocking a proximal end thereof in external groove 237 of bulk of insulation 230, then connector sleeve 175 is bonded to an outer insulation layer of lead body 130, for example, with a silicone medical adhesive. Connector sleeve 175 isolates the couplings from the environment external to lead 100, and may provide a degree of strain relief between lead body 130 and fitting 730. However, a transition fitting that provides additional strain relief may be substituted for fitting 730, according to some alternate embodiments, for example, as shown in FIGS. 8 and 9.

Figure 8:
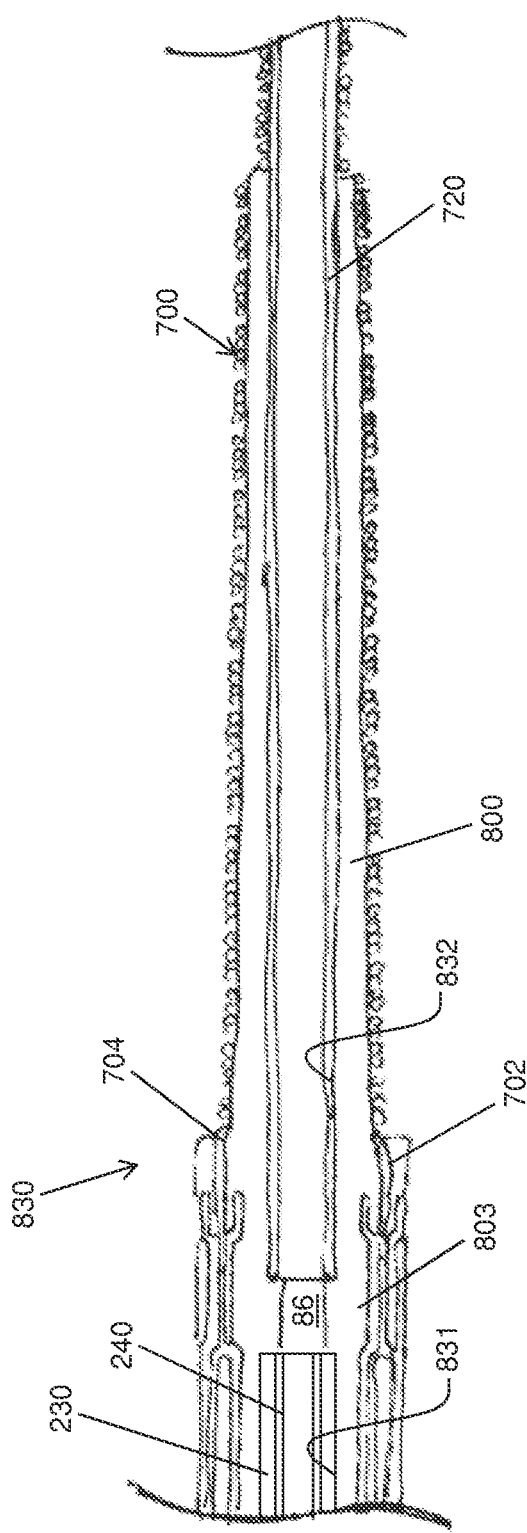
FIG. 8 is a cross-section view through a transition fitting portion of a lead connector assembly, according to some alternate embodiments.
Figure 9:
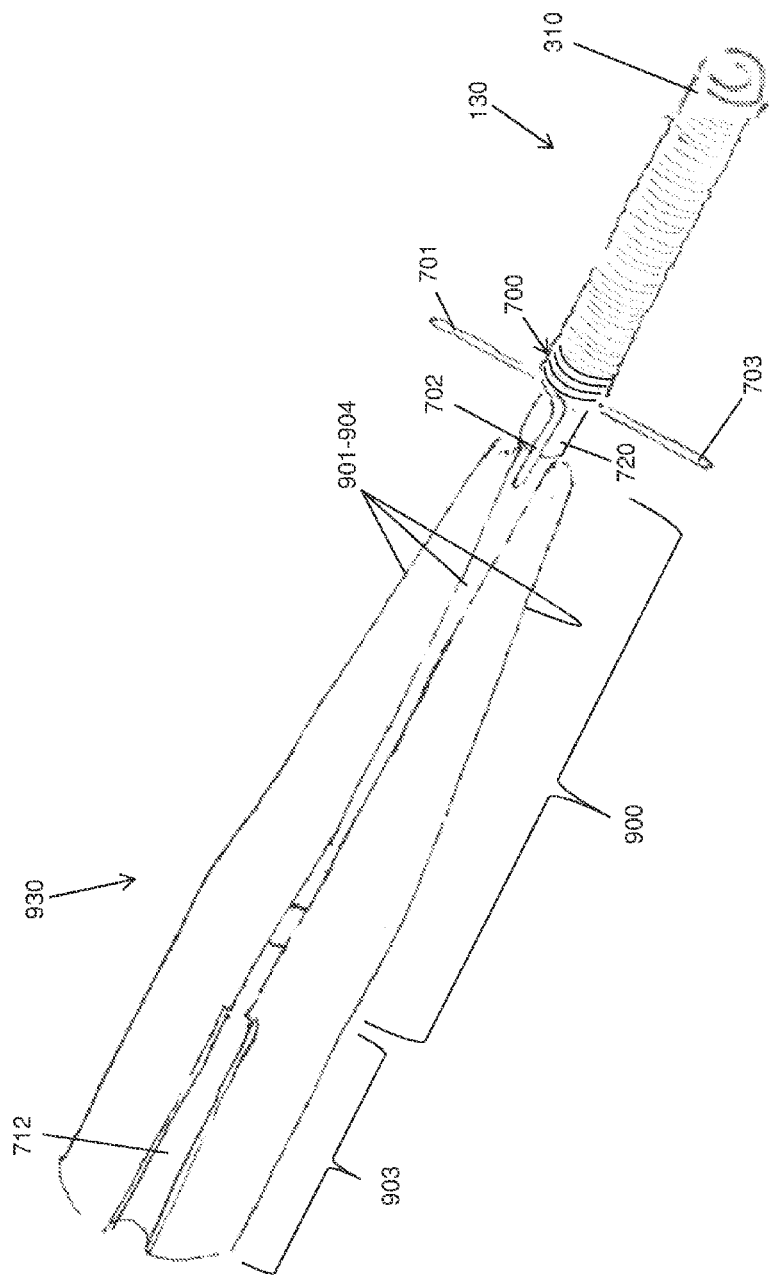
FIG. 9 is a perspective view of another transition fitting, according to yet further embodiments, positioned adjacent a lead body for assembly therewith.

FIG. 8 is a cross-section view through a transition fitting 830 of a lead connector assembly, according to some alternate embodiments; and FIG. 9 is a perspective view of another transition fitting 930, according to yet further embodiments, positioned adjacent to lead body 130 for assembly therewith. FIG. 8 illustrates transition fitting 830 including a grooved portion 803, which is similar to transition fitting 730, and a strain relief portion 800, which extends distally from grooved portion 803, and which has a tapered profile about which multi-conductor coil 700 is fitted. FIG. 8 further illustrates a lumen 86 of transition fitting 830 including a proximal portion 831, similar to proximal portion 731 of lumen 76 of fitting 730, and a distal portion 832; distal ends 232, 242 of insulative bulk 230 and conductive core 240, respectively, of assembly 200 (FIG. 2A) are fitted with proximal portion 831 of lumen 86, and inner insulation tubing 720 is fitted within distal portion 832 of lumen 86 such that strain relief portion 800 of fitting 830 is sandwiched between inner insulation tubing 720 and coil 700. FIG. 9 illustrates transition fitting 930 including a grooved portion 903, which is similar to transition fitting 730, and a strain relief portion 900, which extends distally from grooved portion 903, and which has slots 901-904 formed therein. According to the illustrated embodiment, strain relief portion 900 is sized to fit around inner insulation tubing 720, multi-conductor coil 700, and an outer insulation tubing 310 of lead body 130, which overlays coil 700; and each slot 901-904 allows a corresponding conductor coil filar 701-704 to be received in a corresponding groove 711-714 of grooved portion 903, as lead body 130 is assembled together with fitting 930, as can be seen for conductor 702 in FIG. 9. Although not shown, it should be understood that a lumen of transition fitting 930 includes a proximal portion similar to that of transition fitting 730 to join with assembly 200.

In the foregoing detailed description, the invention has been described with reference to specific embodiments. However, it may be appreciated that various modifications and changes can be made without departing from the scope of the invention as set forth in the appended claims.

The invention claimed is:

1. An assembly for a connector of an implantable medical electrical lead, the assembly having a uniform outer diameter conforming to a requirement for the lead connector to mate with a connector receptacle of an implantable medical device, and the assembly comprising:

a conductive core extending from a proximal end thereof to a distal end thereof, along a central longitudinal axis of the assembly;

three contact rings extending around the conductive core and spaced apart from one another along a length of the core, each of the rings having an inner surface, and an outer contact surface, each outer contact surface defining the uniform outer diameter;

four conductor pins, each pin extending from a proximal end thereof to a distal end thereof, alongside the conductive core, the proximal end of a first pin of the four conductor pins being coupled to the inner surface of a first ring of the three contact rings, the proximal end of a second pin of the four conductor pins being coupled to the inner surface of a second ring of the three contact rings, the proximal end of a third pin of the four conductor pins being coupled to the inner surface of a third ring of the three contact rings, the proximal end of a fourth pin of the four conductor pins being coupled to an outer surface of the conductive core, and the fourth pin having a bend formed therein, the bend being located between the proximal end of the fourth pin and a remainder of the pin such that the remainder is spaced outward from the outer surface of the conductive core; and a bulk of insulation extending around the conductive core and the four conductor pins, and extending proximal to, and distal to the three contact rings, and extending between the three contact rings, the bulk of insulation including an outer surface divided into a first, second, third, and fourth sealing surfaces, the first sealing surface extending proximally from the first ring to a proximal end of the assembly, the second sealing surface extending between the first and second rings, the third sealing surface extending between the second and third rings, the fourth sealing surface extending distally from the third ring, each sealing surface also defining the uniform outer diameter of the assembly; and wherein the distal end of each conductor pin protrudes distally from the bulk of insulation; and the distal ends of the conductor pins are spaced apart from one another, and spaced approximately equidistant from the central longitudinal axis.

2. The assembly of claim 1, wherein each of the first, second, and third conductor pins has a bend formed therein, each bend being located between the proximal end and a remainder of the corresponding pin, such that each remainder is spaced inward from the inner surface of the corresponding contact ring.

3. The assembly of claim 1, further comprising a lumen extending from the proximal end of the assembly to a distal end of the assembly, and along the central longitudinal axis, the lumen being defined, at least in part, by the conductive core.

4. The assembly of claim 1, wherein the proximal end of the conductive core defines a lumen; and further comprising a multi-point contact mounted within the lumen, the multi-point contact being configured to engage with a terminal connector pin of the lead connector.

5. The assembly of claim 1, wherein the proximal end of the conductive core defines a lumen; and further comprising a multi-point contact mounted within the lumen, the multi-point contact being configured to engage with a terminal connector pin of the lead connector.

6. The assembly of claim 5, wherein an entirety of the multi-point contact is contained within the lumen of the conductive core and engages the terminal connector pin therein.

7. The assembly of claim 5, wherein a distal portion of the multi-point contact is contained within the lumen of the conductive core, and a proximal portion of the multi-point contact extends proximally from the conductive core, the proximal portion engaging the terminal connector pin.

8. The assembly of claim 1, further comprising a transition fitting joined to the bulk of insulation, the fitting comprising a lumen and four peripheral grooves; and wherein:
the lumen of the transition fitting has a proximal portion, in which the distal end of the conductive core extends, and a distal portion, which is sized to receive an inner portion of a body of the lead;

each groove of the transition fitting supports the distal end of a corresponding conductor pin; and each groove of the transition fitting is sized to receive a corresponding conductor of a plurality of conductors of the body of the lead, such that each conductor pin of the assembly can be coupled to the corresponding lead conductor within the corresponding groove, when the inner portion of the lead body is received in the lumen of the fitting.

9. The assembly of claim 8, wherein:
the proximal portion of the lumen of the transition fitting has an asymmetric profile; and a distal end of the bulk of insulation extends around the distal end of the conductive core, the distal end of the bulk of insulation having an asymmetric outer profile that mates with the asymmetric profile of the proximal portion of the lumen of the transition fitting.

10. The assembly of claim 8, wherein the transition fitting further comprises a strain relief portion extending distally from the grooves, the distal portion of the lumen of the fitting extending within the strain relief portion, and the strain relief portion being sized to fit between the inner portion of the lead body and the plurality of conductors of the lead body, when the inner portion is received in the lumen of the fitting, and each conductor of the plurality of conductors is received in the corresponding groove of the fitting.

11. The assembly of claim 8, wherein:
the transition fitting further comprises a strain relief portion extending distally from the grooves, the strain relief portion including a plurality of longitudinal slots, each slot aligned with a corresponding groove and extending therefrom to an open end at a distal end of the fitting;

the distal portion of the lumen of the fitting extends within the strain relief portion; and the strain relief portion is sized to fit around the inner portion of the lead body, the plurality of conductors of the lead body, and an outer insulation layer of the lead body, which overlays the plurality of conductors, when the inner portion is received in the lumen, and each conductor of the plurality of conductors is received in the corresponding groove, via the corresponding slot.

12. A connector for an implantable medical electrical lead, the connector having a uniform outer diameter conforming to a requirement for the lead connector to mate with a connector receptacle of an implantable medical device, and the connector comprising:

a core circuit comprising a conductive core, a terminal connector pin, and a conductor pin, the conductive core extending from a proximal end thereof to a distal end thereof, along a central longitudinal axis of the connector, the conductor pin extending from a proximal end thereof to a distal end thereof, the proximal end of the conductor pin being coupled to an outer surface of the conductive core, and the conductor pin having a bend formed therein, the bend being located between the proximal end of the conductor pin and a remainder of the conductor pin such that the remainder is spaced outward from the outer surface of the conductive core, and the terminal connector pin including a shank coupled to the proximal end of the conductive core;

at least one contact circuit, each contact circuit comprising a contact ring and a conductor pin, each contact ring extending around the conductive core and including an outer contact surface that defines the uniform outer diameter of the connector, and each conductor pin extending between a proximal end thereof and a distal end thereof, the proximal end of each conductor pin of the at least one contact circuit being coupled to an inner surface of a corresponding contact ring; and a bulk of insulation extending around the conductive core and the conductor pins of the core circuit and the contact circuit, the bulk of insulation including an outer surface divided into at least two sealing surfaces, a first of the at least two sealing surfaces extending proximally from one of the contact rings, and a second of the at least two sealing surfaces extending distally from the same contact ring, the at least two sealing surfaces further defining the uniform outer diameter of the connector; and wherein the terminal connector pin protrudes proximally from the bulk of insulation and defines a proximal end of the connector;

the distal end of each conductor pin protrudes distally from the bulk of insulation; and the distal ends of the conductor pins are spaced apart from one another and spaced approximately equidistant from the central longitudinal axis.

13. The connector of claim 12, wherein each conductor pin of the at least one contact circuit has a bend formed therein, each bend being located between the proximal end and a remainder of the corresponding pin, such that each remainder is spaced inward from the inner surface of the corresponding contact ring.

14. The connector of claim 12, further comprising a lumen extending from the proximal end of the connector to a distal end of the connector, and along the central longitudinal axis, the lumen being defined, at least in part, by the terminal connector pin and the conductive core.

15. The connector of claim 12, wherein the proximal end of the conductive core is recessed within the bulk of insulation and spaced distally from the proximal end of the connector.

16. The connector of claim 12, wherein:
the at least one contact circuit comprises a first contact circuit, a second contact circuit, and a third contact circuit; and
the at least two sealing surfaces of the bulk of insulation comprises four sealing surfaces, the first sealing surface extending proximally from the first contact ring of the first contact circuit, the second sealing surface extending between the first contact ring and a second contact ring of the second contact circuit, the third sealing surface extending between the second contact ring and a third contact ring of the third contact circuit, and the fourth sealing surface extending distally from the third contact ring.

17. The connector of claim 12, wherein the proximal end of the conductive core defines a lumen; and further comprising a multi-point contact mounted within the lumen, the multi-point contact engaging the shank of the terminal connector pin.

18. The connector of claim 17, wherein an entirety of the multi-point contact is contained within the lumen of the conductive core and engages the terminal connector pin therein.

19. The connector of claim 17, wherein a distal portion of the multi-point contact is contained within the lumen of the conductive core, and a proximal portion of the multi-point contact extends proximally from the conductive core, the proximal portion engaging the terminal connector pin.

20. The connector of claim 12, further comprising a transition fitting joined to the bulk of insulation, the fitting comprising a lumen and four peripheral grooves; and wherein:
the lumen of the transition fitting has a proximal portion, in which the distal end of the conductive core extends, and a distal portion, which is sized to receive an inner portion of a body of the lead;
each groove of the transition fitting supports the distal end of a corresponding conductor pin; and
each groove of the transition fitting is sized to receive a corresponding conductor of a plurality of conductors of the body of the lead, such that each conductor pin of the connector can be coupled to the corresponding lead conductor within the corresponding groove, when the inner portion of the lead body is received in the lumen of the fitting.

21. The connector of claim 20, wherein:
the proximal portion of the lumen of the transition fitting has an asymmetric profile; and
a distal end of the bulk of insulation extends around the distal end of the conductive core, the distal end of the bulk of insulation having an asymmetric outer profile that mates with the asymmetric profile of the proximal portion of the lumen of the transition fitting.

22. The connector of claim 20, wherein the transition fitting further comprises a strain relief portion extending distally from the grooves, the distal portion of the lumen of the fitting extending within the strain relief portion, and the strain relief portion being sized to fit between the inner portion of the lead body and the plurality of conductors of the lead body, when the inner portion is received in the lumen of the fitting, and each conductor of the plurality of conductors is received in the corresponding groove of the fitting.

23. The connector of claim 20, wherein:
the transition fitting further comprises a strain relief portion extending distally from the grooves, the strain relief portion including a plurality of longitudinal slots, each slot aligned with a corresponding groove and extending therefrom to an open end at a distal end of the fitting;
the distal portion of the lumen of the fitting extends within the strain relief portion; and
the strain relief portion is sized to fit around the inner portion of the lead body, the plurality of conductors of the lead body, and an outer insulation layer of the lead body, which overlays the plurality of conductors, when the inner portion is received in the lumen, and each conductor of the plurality of conductors is received in the corresponding groove, via the corresponding slot.

* * * * *